United States Patent [19]
Giovannetti

[11] Patent Number: 5,830,162
[45] Date of Patent: Nov. 3, 1998

[54] APPARATUS FOR THE ANTIGRAVITY MODIFICATION OF THE MYOTENSIONS ADAPTING THE HUMAN POSTURE IN ALL OF THE PLANES OF SPACE

[76] Inventor: Giovanni Battista Giovannetti, Via Peccioli, 18, 00139 Rome, Italy

[21] Appl. No.: 727,315

[22] PCT Filed: Jan. 23, 1993

[86] PCT No.: PCT/IT93/00005

§ 371 Date: Sep. 13, 1994

§ 102(e) Date: Sep. 13, 1994

[87] PCT Pub. No.: WO93/14733

PCT Pub. Date: Aug. 5, 1993

Related U.S. Application Data

[63] Continuation-in-part of Ser. No. 557,675, Nov. 13, 1995, abandoned, which is a continuation of Ser. No. 256,366, Sep. 13, 1994, abandoned.

[30]    Foreign Application Priority Data

Jan. 23, 1992 [IT] Italy ................................ RM92A0051

[51] Int. Cl.$^6$ ..................................................... A61H 1/00
[52] U.S. Cl. ................................ 601/23; 482/69; 602/32; 602/36
[58] Field of Search ........................ 602/32–36; 606/241; 601/23, 26, 33–35; 600/592, 594, 595; 23/172; 482/51, 54, 56, 69; 434/258; 5/86.1, 89.1

[56]    References Cited

U.S. PATENT DOCUMENTS

| 3,778,052 | 12/1973 | Andow et al. | 482/69 |
| 3,894,437 | 7/1975 | Hagy et al. | 73/172 |
| 4,122,840 | 10/1978 | Tsuchiya et al. | 128/779 |
| 4,416,293 | 11/1983 | Anderson et al. | 128/779 |
| 4,928,708 | 5/1990 | Landwehr et al. | 128/779 |
| 4,973,044 | 11/1990 | Jones | 482/69 |
| 5,050,590 | 9/1991 | Futakami | 482/69 |
| 5,080,109 | 1/1992 | Arme, Jr. | 600/595 |
| 5,088,504 | 2/1992 | Benesh et al. | 600/594 |
| 5,192,305 | 3/1993 | Sastre | 606/241 |
| 5,273,502 | 12/1993 | Kelsey et al. | 482/69 |
| 5,311,880 | 5/1994 | Lancaster et al. | 600/595 |
| 5,388,591 | 2/1995 | De Luca et al. | 128/779 |
| 5,623,944 | 4/1997 | Nashner | 600/592 |

FOREIGN PATENT DOCUMENTS

| 0002188 | 6/1979 | European Pat. Off. . |
| 2252108 | 6/1975 | France . |
| 2151933 | 12/1972 | Germany . |
| 9017709 | 9/1991 | Germany . |

OTHER PUBLICATIONS

Biomedizinische Technix, vol. 32, No. 10, Oct. 1987, Berlin, pp. 250–254. G. A. Hortsman, et al "A Special Treadmill for the Investigation of Standing and walking in Research and Hospital".

*Primary Examiner*—Jeanne M. Clark
*Attorney, Agent, or Firm*—Stevens, Davis, Miller & Mosher, L.L.P.

[57]    ABSTRACT

A diagnostic and therapeutic apparatus for re-educating the posture of the backbone includes in combination mechanism for controlling the orthostatic posture of the patient, mechanism for carrying out a differential traction on the same patient at different levels in order to cancel out all or a part of his weight, mechanism for correcting the postural defects in the three planes of the space and for blocking the patient within postural limits in order to prevent him from assuming postures other than that therapeutic even during the deambulation. In particular, the orthostatic posture is controlled by measuring the weight resting on each foot of the patient through footboards (19A,19B) sensitive to changes in pressure placed under a travelling band (18), and the traction mechanism are lacings or traction slings (24) slidable around pulleys (22) carried by a rigid framework and put under tension manually by the operator or automatically by a microprocessor receiving data measured from the footboard (19A,19B) sensitive to changes in pressure.

14 Claims, 5 Drawing Sheets

APPARATUS FOR THE ANTIGRAVITY MODIFICATION OF THE MYOTENSIONS ADAPTING THE HUMAN POSTURE IN ALL OF THE PLANES OF SPACE

This application is a Continuation-in-Part of application Ser. No. 08/557,675 (now abandoned), which in turn is a Continuation of application Ser. No. 08/256,366, filed Sep. 13, 1994 (now abandoned), which in turn is a 35 U.S.C. 371 filing of PCT/IT93/00005, filed Jan. 22, 1993 (now abandoned).

The present invention relates to an apparatus for re-educating the posture of the backbone of an individual in all of the three plane of the space, i.e. frontal, sagittal, and transversal, thus avoiding the posture defects and all of the pathological consequences arising therefrom, under antigravity, dynamic conditions and through deambulation on a travelling band.

As known, the weight of the human body is supported by the skeleton, muscles, ligaments, and fasciae. The line representing that weight goes down from above along the backbone, bifurcates at the third lumbar vertebra, turns to the two opposite coxae (hip-joints), goes down along the lower limbs and goes up again by the same way until it rejoins at the centre of the pubic bone to form a closed loop of forces. However, skeleton is very seldom postured in a physiologically correct way so as to absorb the most of the weight of the human body. Actually men assume comfort postures or postural bad habits requiring the aid of supports constituted by muscular tensions, fasciae, and ligaments to restore the balance. Such "dynamic compensations" of a "static defect" become permanent in time such as to constitute a pseudo scheme of movement (the automatic total scheme of movements) that, even if it is not physiologically correct, becomes definitively functional, thus causing pathologic modifications in capsules, ligaments and joint surfaces and occurrences of aches and pains of different nature and intensity. The physiatrics is aware of such problem for some time so that several equipment have been manufactured to try to solve it. The latter, however, have never considered the "global problem", i.e. the functional and dynamic whole of the human body.

From FR-A-2 252 108 it is known an apparatus for re-education of the human backbone comprising means for carrying out differential traction at different levels, means for correcting the postural defects and for blocking the patient and means for allowing the patient to walk. However this apparatus does not permit both a diagnostics investigations of postural defects and a programmed treatment since there is no means of monitoring the orthostatic position of the patient. It is already known from the Biomedizinische Technik Vol. 32 October 1987, the possibility to control the weight resting on each patient's foot lying on a footboards to investigate the standing and walking motor control and to value neuromuscular diseases without the possibility of corrections.

The present invention seeks to overcome the limits of the existing apparatus and to provide an apparatus by which the correction of postural bad habits upstream of the several peripheral symptoms which can occur in different ways becomes total, permanent, spontaneous and directed in all of the three planes of the space. The inventive concept of the present invention is of providing an apparatus by which the patient can be subjected to differential tractions at different levels by cancelling out all or a part of his weight and effecting a number of successive corrections such as to force the patient to assume a correct posture in the frontal, sagittal, and transversal planes in static attitude, and by forcing the patient to keep such posture even in dynamic attitude, i.e. during the deambulation, until he reaches stably and definitively a new correct total scheme of movements, while keeping the orthostatic position of the patient under continuous monitoring.

According to the invention this can be achieved by continuously monitoring the weight resting on either patient's foot whose unbalance shows postural defects of the subject or alternately by detecting the displacements of reference points of the patient's body with respect to an ideal line.

Therefore, the present invention provides according to a first aspect thereof a diagnostic and therapeutic apparatus for re-educating the posture of the backbone which includes in combination means for measuring the orthostatic posture of the patient by measuring the weight resting on each patient's foot, means for carrying out a differential traction on the same patient at different levels in order to cancel out all or a part of his weight, means for correcting the postural defects by leading the patient again to the respect of the symmetries in the three planes of the space and for blocking the patient within postural limits inside which he is free but from which he cannot come out, means for allowing the patient to walk in his tridimensionally corrected hanging posture in order to force him to the new automatic scheme of movements adapted to the incidental situation.

Another object of the invention is to provide an apparatus as described above, wherein the means for controlling the weight resting on each foot supplies data to a microprocessor adapted to automatically control the operation of the traction means for leading the patient again to a predetermined postural attitude. A further object of the invention is to provide an apparatus as described above, wherein the data of the displays is transmitted to a computer adapted to store the data of the beginning and the end of the treatment and to issue a graphic representation of the same. Still another object of the invention is to provide an apparatus including, instead of the means for measuring the patient's weight, optical and/or electronic means for detecting the spatial variation of the position of a reference point attached to the patient's body.

According to a first preferred embodiment the apparatus of the present invention includes in combination a travelling band for the deambulation provided with two footboards sensitive to changes in pressure and adapted to indicate on a display the weight resting on each foot of the patient standing thereon, and a rigid framework which can be firmly anchored to the floor and/or to the ceiling of the operational room above said travelling band, and to which the patient is secured by a number of traction slings fastened to five suspension points, e.g. pulleys. Such slings allow both the displayed data to be set, i.e. the weight resting on both feet to be compensated, and such weight to be partially released in a symmetric way at different levels so as to display the wrong postural attitudes of the patient through the loss of the previously reached balance between the weights resting on the two feet.

The apparatus also includes a number of movable arms provided with retainers or stops to be applied to the patient's body at different (pelvic, sacral, sternal, humeral and dorsal) levels in order to prevent him from assuming postures different from those therapeutic even during the deambulation. According to a preferred embodiment such retainers consist of oleodynamic pistons assembled in suitable hydraulically driven structures and controlled for an optimum positioning.

The description of the invention will be better understood with reference to the accompanying drawings which illustrate only by way of a non-limitative example a preferred embodiment thereof. In the drawings.

Figure 1:
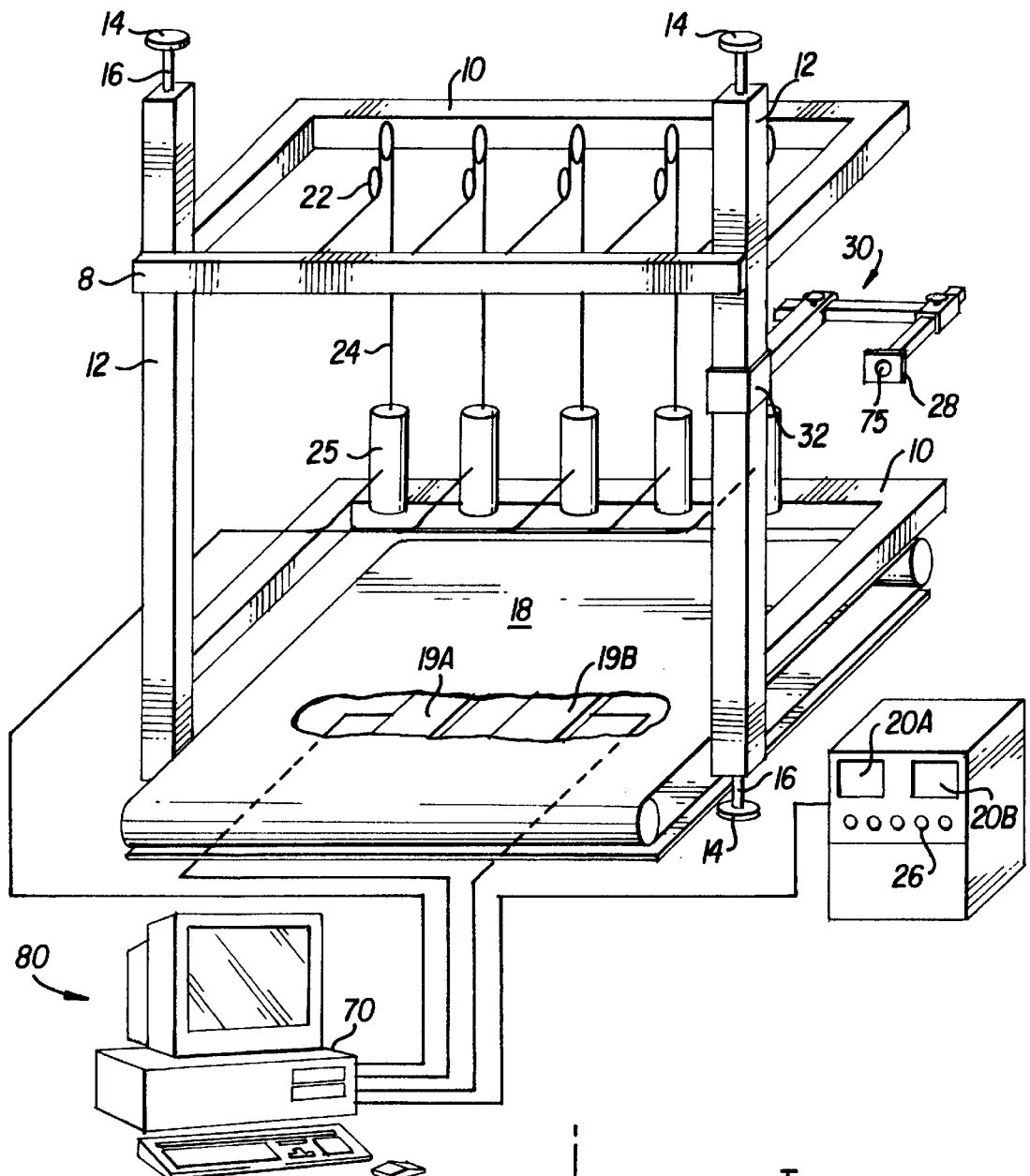
FIG. 1 is a perspective view of the apparatus of the invention.
Figure 2:
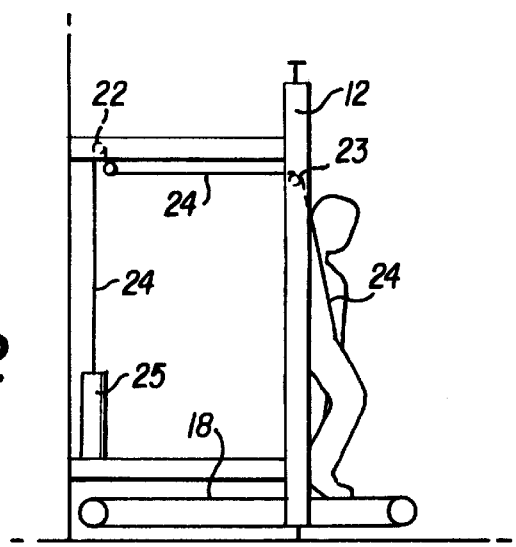
FIG. 2 is a schematic elevation side view of the same.
Figure 3:
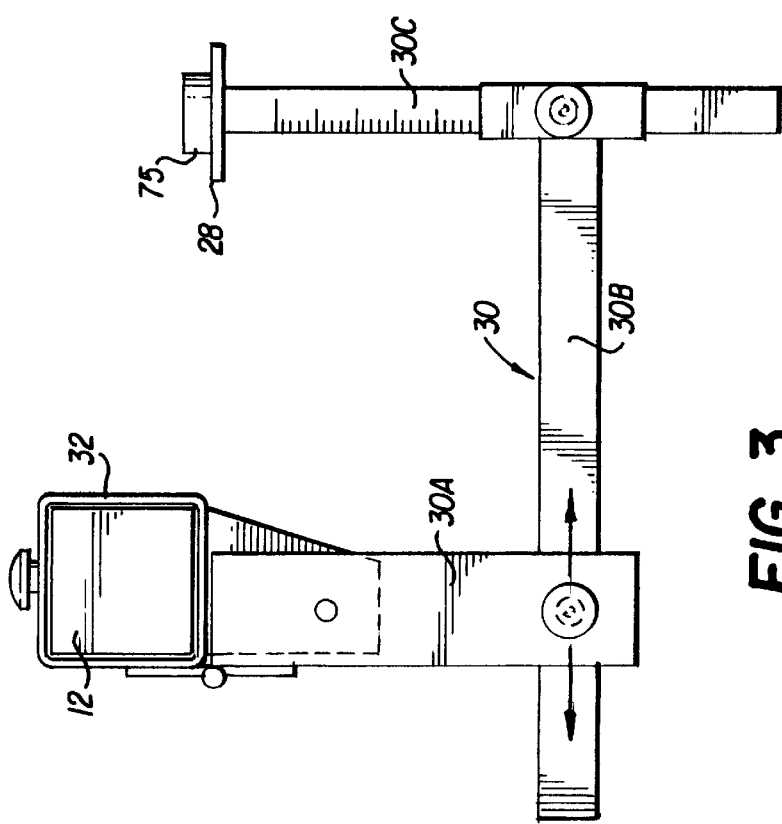
FIG. 3 is a plan view of a detail of one arm provided with retainers.

With reference to FIGS. 1 to 3 the apparatus includes a bridge framework of tubular metal sections formed by a front beam 8, a rear beam or a pair of rear beams 10, and two uprights 12 extending from the floor to the ceiling of the operational room and secured thereto by mutual abutment of pressure discs 14 adjustable through threaded pins 16 without drilling or permanent securing devices. A travelling band 18 for deambulation having a varying resistance is placed between the two uprights 12 on two footboards or load cells 19A and 19B sensitive to changes in pressure and each adapted to transmit to a corresponding display 20A and 20B and to a microprocessor 70, the weight resting on each patient's foot. Microprocessor 70 is contained in an electronic central processing unit 80 which controls automatically the operation of traction means 24, 25. Attached to the rear beam 10 are a certain number (five in the illustrated example) of pulleys 22 around which traction lacings 24 are wound which are subjected to tension by devices 25 of the known type such as electric or hydraulic pistons, counterweight systems of conventional mechanical (rocker arm) or hydraulic type, or other equivalent systems shown only schematically. The traction values are displayed by suitable indicators 26 to the operator. Such lacings pass around pulleys 23 of front beam 8 and are provided with the ordinary accessories used in the traction techniques such as traction bands and slings, length regulators, etc. The apparatus is also provided with a number of rigid retainers or stops 28 to be positioned against the patient's body for blocking in the posture forced by the correction traction means, said stops 28 being provided with pressure sensors (75) for measuring the thrust of the patient. Such retainers are carried by horizontal arms 30 which can vertically slide along uprights 12 by means of sleeves 32 and be adjusted in their lengths as they are formed of several pieces 30A, 30B and 30C slidable perpendicularly to one another. The arms may be scaled as shown in 30C to determine the displacement in the position of the arms and stops 28 as treatment progresses. The described apparatus has both diagnostic and therapeutic functions. It is thereby possible to show first of all the comfort postures or postural defects of the subject and then to lead the same subject to take on correct postures which becomes stable and definitive as the therapy proceeds.

It is now disclosed by way of example the treatment of a subject having five suspension points, and namely: one at the cranium, two at the thorax, and two at the ischium (inguen).

The patient is placed on a motorized travelling band or a sliding band 18 with his feet resting exactly on the corresponding footboards sensing the weight. The right display 20A shows the weight resting as a whole on the right foot at 19A and the left display 20B shows the weight resting as a whole on the left foot at 193. Such weights are almost always different from each other because the total weight divides equally very seldom but rests more on the right side or the left side than the other side according to the importance of the posture defect to be corrected.

The right or left ischiatic suspension acts for levelling the values of the two displays 20A and 20B through the corresponding traction lacing 24. This operation aims at balancing the pelvis to avoid resting defects on one side or on the other side.

Now a symmetrical thoracic traction, i.e. a balanced weight release on the right and left sides, is carried out in order to compensate about 20% of the body weight. The preceding values of displays 20A and 20B are very likely varied at the end of such operation. Actually, if the subject had, for example, a posture of the trunk inclined to the right side due to the rotation of the backbone or to the retraction of the muscles responsible for that movement towards that side, the indifferentiated upwards traction of the trunk will raise the pelvis on that side and will deduct a weight equal to the intensity and amplitude of the postural lack of balance.

The traction is then differentiated by means of a lateral thoracic traction lacing 24 so as to compensate for the values of displays 20A and 20B.

Finally, a light cervical traction is carried out for excluding the weight of the cranium: the patient is then subjected to differential tractions at several levels, the intensity thereof expressing the existing myofascial reactions.

The pelvic, sacral, sternal, humeral and dorsal retainers or stops 28 are then positioned against the patient's body in order to discourage any attempt of compensation by an attitude other than that forced by the correcting tractions. Patient is invited to walk by setting a very low resistance at the beginning. It is self-evident that under such conditions the patient cannot make use of his usual (and wrong) scheme of deambulation as:

his proprioceptive sensations of his own weight are deeply changed and then he cannot make use of his usual scheme of movement;

the attempts of compensation made by the assumption of different, less tiring, comfort postures are cancelled by the differential tractions of lacings 24 and by stops 28 fixing the therapeutic posture.

Any pressure sensor 75 on stops 28 can display the different thrusts of the several points of the body and then the attitude against a back thrust which rotates the backbone.

Under such conditions the patient is forced to invent a new way of movement and shall do this by using skeleton, muscles, etc. which are now correctly postured. If at the beginning the patient moves with extreme difficulty, as the therapy proceeds the patient will stably reach a new global, now correct scheme of movement. The displays can translate into objective data the progress of the therapy. In fact, as the therapy proceeds and the several defective bends of the backbone and the myofascial reactions are compensated and cancelled, it is as though the trunk of the patient got longer. As a consequence the efficiency of the thoracic traction will be progressively reduced, and the displays will show it by an increase of the weight shown. The responsible personnel can then draw up a hospital file of the patient in which the detected values in the several therapy sessions will be recorded until stable values not subjected to change are reached. Thus a graph as well as digital data of the reached, global and definitive, correct posture can be obtained.

The described apparatus is susceptible to be used in combination with a microprocessor 70 contained in an electronic central processing unit 80, capable of storing data on beginning treatment as well as ending treatment, the evaluation of the differences detected, and data during the treatment for statistical research purposes. It is also possible to use a microprocessor 70 for controlling the function on the basis of a stored program.

Alternatively, the orthostatic posture of the subject can be put under control by detecting the displacement of a reference point of the patient's body in the space. To this purpose a photoelectric cell and a scanner can be used.

Figure 4:
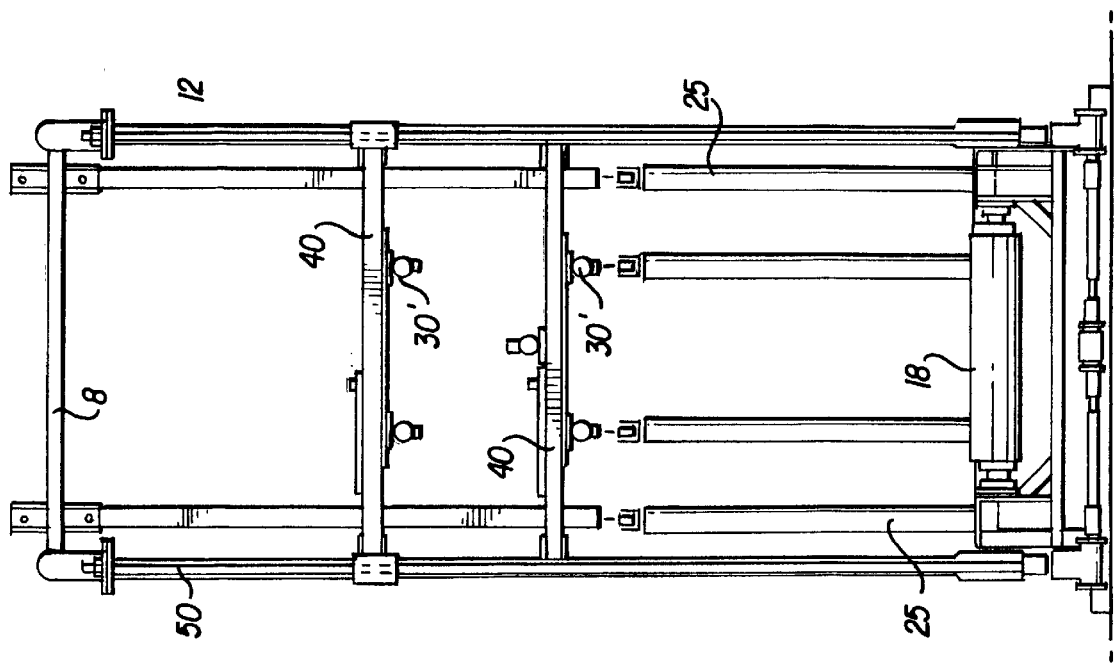
FIG. 4 is a frontal elevational view of a second embodiment of the invention, in which the retainers are oleodynamically driven.
Figure 5:
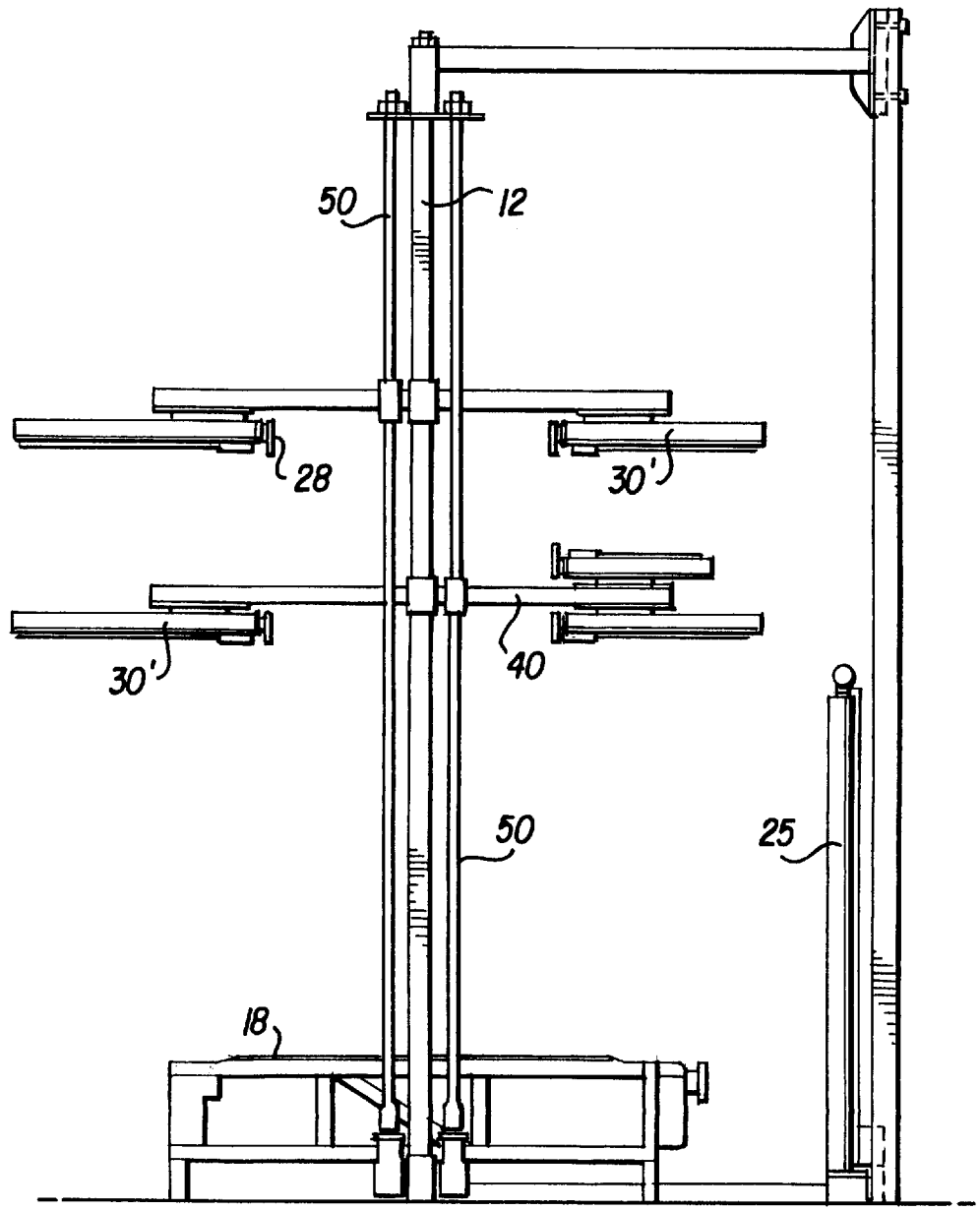
FIG. 5 is a left side elevation view of FIG. 4.
Figure 6:
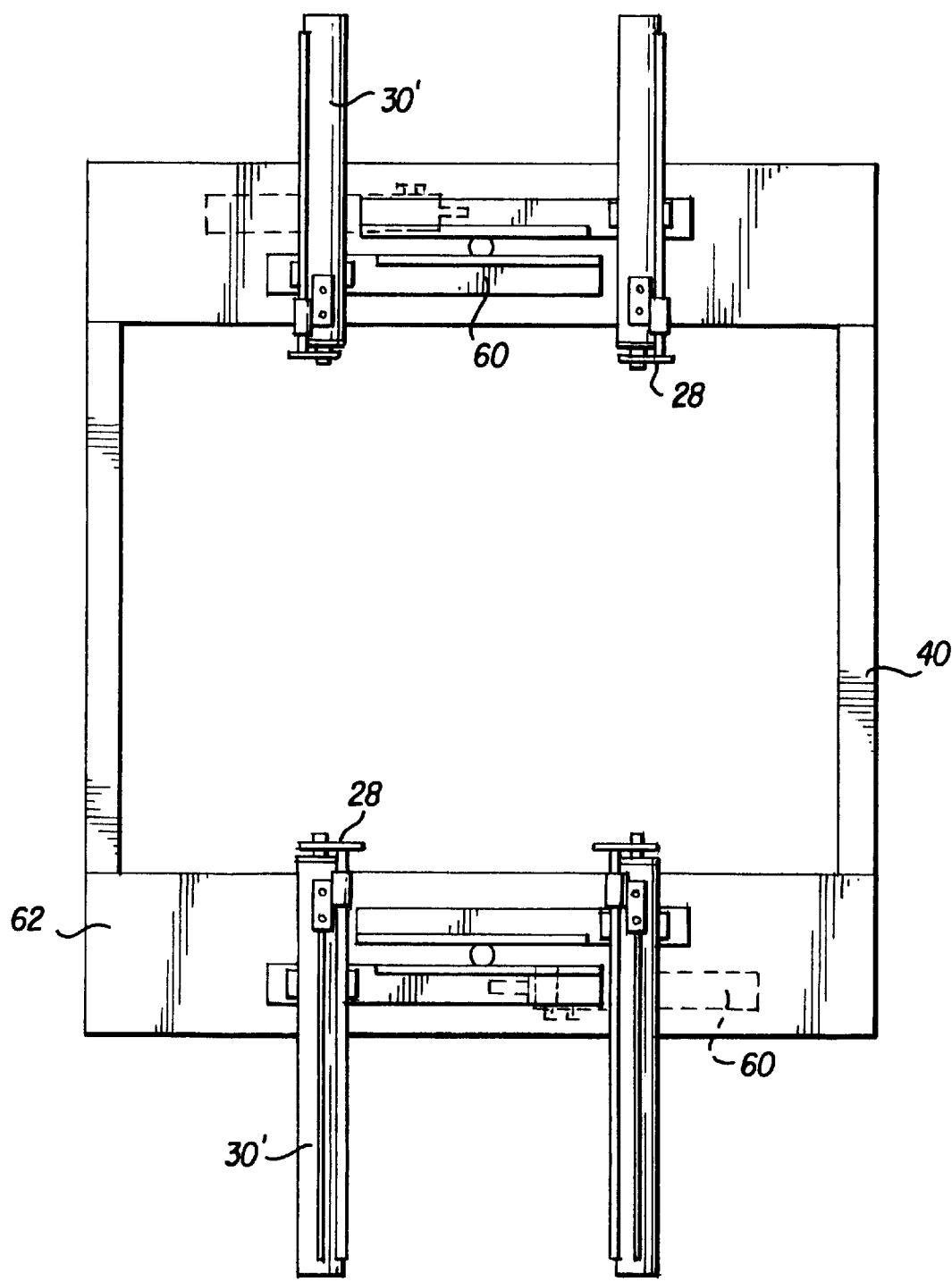
FIG. 6 is a detail of a movable framework where oleodynamic cylinders are provided.
Figure 7:
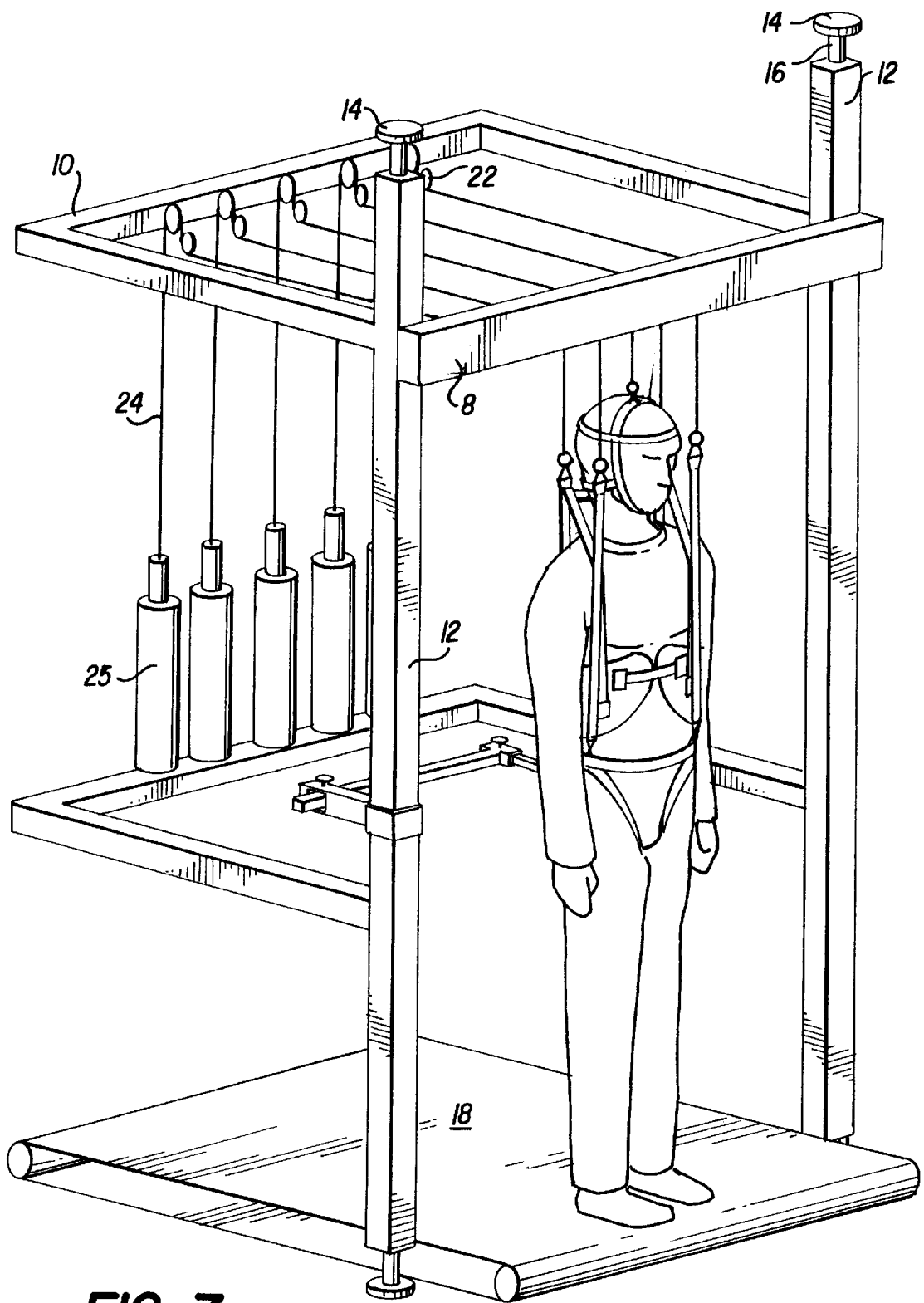
FIG. 7 is a perspective view of the patient having traction lacings attached thereto.

In FIGS. 4 to 6 a second embodiment is shown, in which stops 28 are moved by oleodynamic cylinders 30' carried on frames 40 vertically movable along guides 50 parallel to uprights 12 between which slidable footboard 18 is placed. As can be seen, cylinders 30' can be horizontally displaced on the relative movable frames 40 and approached to or moved away from each other by a further oleodynamic positioning cylinder 60 attached to a proper plate 62.

I claim:

1. A diagnostic and therapeutic apparatus for reeducating the posture of the human backbone comprising, in combination, a frame (8, 10, 12), weight measuring means (19A, 19B) within said frame (8, 10, 12) for monitoring the orthostatic posture of a patient by measuring the weight resting on each foot of a standing or walking patient, traction means (24, 25) mounted on said frame (8, 10, 12) for carrying out a differential traction on the same patient at different levels in order to cancel out all or a part of the patient's weight, blocking means (28, 30, 32) mounted on said frame (8, 10, 12) for correcting the patient's postural defects by forcing the patient to assume correct posture in the frontal, sagittal and transversal planes and for maintaining the patient within postural limits inside which the patient is free to move but from which the patient cannot come out, an endless walking means (18) for allowing the patient to walk in a tridimensionally corrected hanging posture in order to force the patient to a new automatic scheme of movements adapted to the incidental situation, wherein at least a portion of said endless walking means is positioned above said weight measuring means (19A, 19B), and a microprocessor (70) connected to said weight measuring means (19A, 19B) and said traction means (24, 25) controlling automatically the operation of said traction means (24, 25), said weight measuring means (19A, 19B) feeding data to said microprocessor (70) to control automatically the operation of the traction means (24, 25) for leading the patient to a predetermined postural scheme.

wherein said traction means includes multiple traction slings that are independently attached to a means for independently adjusting the tension in each sling according to the control signal of the microprocessor as to maintain the patient in the desired posture.

2. The diagnostic and therapeutic apparatus as claimed in claim 1, wherein said weight measuring means (19A, 19B) are footboards sensitive to changes in pressure placed under said endless walking means and wherein said endless walking means is a motorized travelling band.

3. The diagnostic and therapeutic apparatus as claimed in claim 1, wherein said weight measuring means (19A, 19B) are footboards sensitive to changes in pressure placed under said endless walking means and wherein said endless walking means is a slidable band.

4. The diagnostic and therapeutic apparatus as claimed in claim 1, wherein said weight measuring means (19A, 19B) are load cells sensitive to changes in pressure placed under said endless walking means and wherein said endless walking means is a motorized travelling band.

5. The diagnostic and therapeutic apparatus as claimed in claim 1, wherein said weight measuring means (19A, 19B) are load cells sensitive to changes in pressure placed under said endless walking means and wherein said endless walking means is a slidable band.

6. The diagnostic and therapeutic apparatus as claimed in claim 1, further including pulleys (22) and wherein said traction means being attachable at one end to the patient and at another end to said means for independently adjusting the tension, said pulleys (22) being mounted on said frame (8, 10, 12) around which said slings (24) slide.

7. The diagnostic and therapeutic apparatus as claimed in claim 6, wherein said traction slings (24) are five in number and attached to the patient at five suspension points, wherein one of the suspension points is at the cranium, two of the suspension points are at the thorax, and two of the suspension points are at the ischium (inguen).

8. The diagnostic and therapeutic apparatus as claimed in claim 6, wherein said blocking means (28, 30, 32) include sleeves (32) slidable on vertically shiftable and adjustable rigid support arms (30) and a number of stops (28) which are placeable against the patient's body at predetermined points, said stops (28) being mounted on said vertically shiftable and adjustable rigid support arms (30) slidable by means of sleeves (32) along said frame (8, 10, 12).

9. The diagnostic and therapeutic apparatus as claimed in claim 8, wherein said stops (28) are provided with pressure sensors (75) for measuring the thrust of the patient.

10. The diagnostic and therapeutic apparatus as claimed in claim 1, wherein said blocking means include oleodynamic pistons (30'), rigid, hydraulically driven movable support structures (40) to which said pistons (30') are attached and a plurality of stops (28), said stops (28) being carried by said pistons (30').

11. The diagnostic and therapeutic apparatus as claimed in claim 1, wherein said endless walking means (18) is located about said weight measuring means (19A, 19B), the weight measuring means comprises load cells (19A, 19B), and the microprocessor provides means to receive data detected by the load cells (19A, 19B) and the values of the tractions at the several levels of the body during the therapy and plot the whole treatment.

12. The diagnostic and therapeutic apparatus as claimed in claim 10, including slidable arms for supporting said plurality of stops (28) which are placed against the patient's body, and a device for measuring the positions of said slidable arms supporting said plurality of stops (28) which are placed against the patient's body.

13. A diagnostic and therapeutic apparatus for reeducating the posture of the human backbone comprising, in combination, a frame (8, 10, 12), weight measuring means (19A, 19B) within said frame (8, 10, 12) for monitoring the orthostatic posture of a patient by measuring the weight resting on each foot of a standing or walking patient, traction means (24, 25) mounted on said frame (8, 10, 12) for carrying out a differential traction on the same patient at different levels in order to cancel out all or a part of the patient's weight, blocking means (28, 30, 32) mounted on said frame (8, 10, 12) for correcting the patient's postural defects by forcing the patient to assume correct posture in the frontal, sagittal and transversal planes and for maintaining the patient within postural limits inside which the patient is free to move but from which the patient cannot come out, an endless walking means (18) for allowing the patient to walk in a tridimensionally corrected hanging posture in order to force the patient to a new automatic scheme of movements adapted to the incidental situation, wherein at least a portion of said endless walking means is positioned above said weight measuring means (19A, 19B), and a microprocessor (70) connected to said weight measuring means (19A, 19B) and said traction means (24, 25) controlling automatically the operation of said traction means (24, 25), said weight measuring means (19A, 19B) feeding data to said microprocessor (70) to control automatically the operation of the traction means (24, 25) for leading the patient to a predetermined postural scheme, wherein said blocking means include oleodynamic pistons (30'), rigid, hydraulically driven movable structures (40) to which said pistons (30') are attached and stops (28), said stops (28) being carried by said pistons (30').

14. A diagnostic and therapeutic apparatus for reeducating the posture of the human backbone comprising, in combination, a frame (8, 10, 12), weight measuring means (19A, 19B) within said frame (8, 10, 12) for monitoring the orthostatic posture of a patient by measuring the weight resting on each foot of a standing or walking patient, traction means (24, 25) mounted on said frame (8, 10, 12) for carrying out a differential traction on the same patient at different levels in order to cancel out all or a part of the patient's weight, blocking means (28, 30, 32) mounted on said frame (8, 10, 12) for correcting the patient's postural defects by forcing the patient to assume correct posture in the frontal, sagittal and transversal planes and for maintaining the patient within postural limits inside which the patient is free to move but from which the patient cannot come out, an endless walking means (18) for allowing the patient to walk in a tridimensionally corrected hanging posture in order to force the patient to a new automatic scheme of movements adapted to the incidental situation, wherein at least a portion of said endless walking means is positioned above said weight measuring means (19A, 19B), and a microprocessor (70) connected to said weight measuring means (19A, 19B) and said traction means (24, 25) controlling automatically the operation of said traction means (24, 25), said weight measuring means (19A, 19B) feeding data to said microprocessor (70) to control automatically the operation of the traction means (24, 25) for leading the patient to a predetermined postural scheme, wherein said blocking means include oleodynamic pistons (30'), rigid, hydraulically driven movable structures (40) to which said pistons (30') are attached and stops (28), said stops (28) being carried by said pistons (30') and including slidable arms for supporting said plurality of stops (28) which are placed against the patient's body, and a device for measuring the positions of said slidable arms supporting said plurality of stops (28) which are placed against the patient's body.

\* \* \* \* \*

UNITED STATES PATENT AND TRADEMARK OFFICE
CERTIFICATE OF CORRECTION

PATENT NO. : 5,830,162
DATED : November 3, 1998
INVENTOR(S) : GIOVANNETTI

It is certified that error appears in the above-identified patent and that said Letters Patent is hereby corrected as shown below:

```
Title page, item [22], --item [22] Filed: Oct. 8, 1996--.
Items [86] and [87] should be deleted.
Item [63] after "1994, abandoned" insert
--which is a national stage under 35 U.S.C. 371 of PCT/
IT93/00005, filed on 1/22/93--.
```

Signed and Sealed this

Sixth Day of June, 2000

Attest:

Q. TODD DICKINSON

*Attesting Officer*    *Director of Patents and Trademarks*